United States Patent
Neubert et al.

(10) Patent No.: US 7,091,258 B2
(45) Date of Patent: Aug. 15, 2006

(54) FILLER ON THE BASIS OF PARTICULATE COMPOSITE

(75) Inventors: Roland Neubert, Feldkirch-Tosters (AT); Karin Vogel, Mauren (LI); Ulrich Salz, Lindau (DE); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 10/079,071

(22) Filed: Feb. 20, 2002

(65) Prior Publication Data

US 2002/0152930 A1 Oct. 24, 2002

(30) Foreign Application Priority Data

Feb. 21, 2001 (DE) ................. 101 08 261

(51) Int. Cl.
*A61F 2/00* (2006.01)
*A61L 24/00* (2006.01)
*C08J 3/00* (2006.01)
*C08K 9/04* (2006.01)
*C08L 33/00* (2006.01)

(52) U.S. Cl. ............. 523/113; 433/212.1; 433/222.1; 433/228.1; 523/115; 523/116; 523/117; 523/200; 523/202; 523/205; 523/206; 523/216; 523/217; 524/445; 524/447; 524/431; 524/443; 524/492; 524/493; 524/494; 524/502

(58) Field of Classification Search ........... 523/115, 523/116, 117, 200, 202, 205, 206, 216, 217, 523/113; 524/445, 447, 431, 443, 492, 493, 524/494, 502; 433/212.1, 222.1, 228.1
See application file for complete search history.

(56) References Cited

U.S. PATENT DOCUMENTS

| 4,503,169 A | * | 3/1985 | Randklev ............... 523/117 |
| 4,668,712 A | * | 5/1987 | Hino et al. .............. 522/13 |
| 5,356,951 A | | 10/1994 | Yearn et al. |
| 6,593,395 B1 | | 7/2003 | Angeletakis et al. |
| 2003/0032693 A1 | | 2/2003 | Angeletakis et al. |

FOREIGN PATENT DOCUMENTS

| DE | 1 492 040 | 4/1969 |
| DE | 24 03 211 A1 | 7/1975 |
| DE | 27 05 220 A1 | 8/1977 |
| DE | 30 34 374 A1 | 8/1982 |
| DE | 35 02 594 A1 | 7/1986 |
| DE | 40 04 678 A1 | 8/1991 |
| DE | 43 00 693 A1 | 7/1993 |
| DE | 199 18 974 A1 | 12/1999 |
| EP | 0 394 798 A2 | 10/1990 |
| EP | 0 475 239 A3 | 3/1992 |
| EP | 0 806 458 B1 | 10/1999 |
| EP | 0 983 762 A1 | 3/2000 |
| WO | WO 99/65453 | 12/1999 |
| WO | WO 00/61073 | 10/2000 |

* cited by examiner

*Primary Examiner*—Patrick D. Niland
(74) *Attorney, Agent, or Firm*—Nixon Peabody LLP

(57) ABSTRACT

Particulate composite material with an average particle size of 20 to 50 μm and a maximum content of particles with a size of <10 μm of 10 wt.-% and its use for the preparation of dental materials.

32 Claims, 2 Drawing Sheets

FILLER ON THE BASIS OF PARTICULATE COMPOSITE

Figure 1:
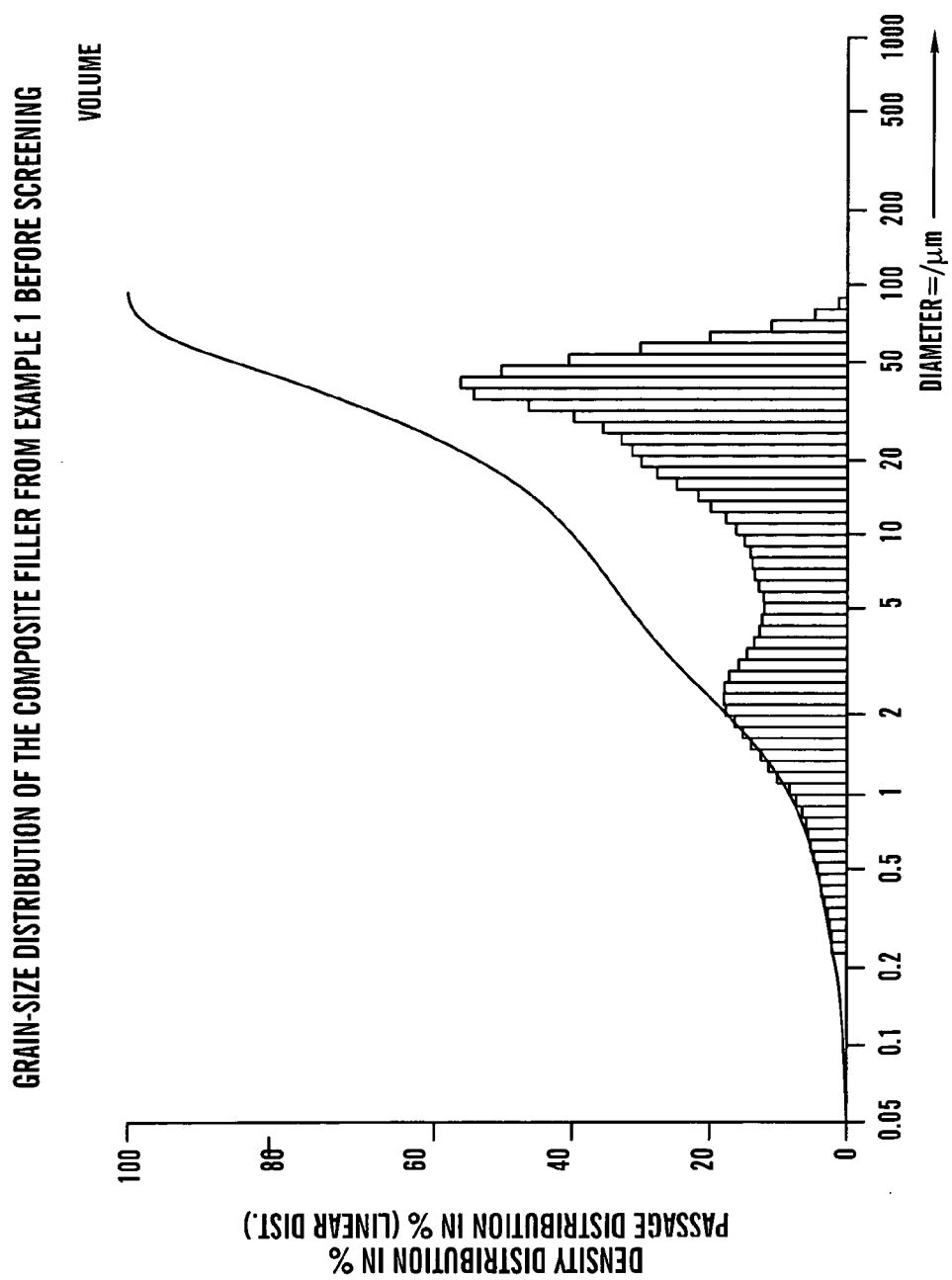

The invention relates to fillers on the basis of particle-shaped composite materials, which have a defined grain size distribution and contain only a small proportion of fine-grain particles.

As a rule, modern dental materials contain a liquid, polymerizable binder in the form of monomers or monomer mixtures as an essential component. It is known that, during the polymerization of such binders, usually a more or less strongly pronounced volume contraction takes place (cf. R. R. Sadhir, R. M. Luck, Expanding Monomers-Synthesis, Characterization and Application; CRC Press, Boca Raton 1992, pages 3ff). The shrinkage is attributable to the development of covalent bonds between the monomer molecules during polymerization, whereby the distance between the molecules is decreased. In the unpolymerized state, the molecules are predominantly held together by Van der Waals forces, which result in a greater intermolecular distance.

During the preparation of pre-shaped parts, the polymerization shrinkage has a very disadvantageous effect on the dimensional stability and the mechanical properties of the moulded bodies. In the case of adhesives and gluing compounds, the polymerization shrinkage adversely affects the adhesion properties and the bonding strength, which deteriorates the adhesion between restoration material and the natural tooth substance of dental materials. Cracks form which encourage the development of secondary caries.

To reduce the polymerization shrinkage of dental materials, the use of high-molecular-weight monomers or pre-polymers, the use of monomers which can be polymerized by ring-opening polymerization, the addition of inert, porous or expanding fillers or gas-releasing systems was described.

When selecting suitable filling materials, particle size assumes special importance. Large particle diameters produce materials with poor polishability and unacceptable abrasion, while filling materials having a small particle size show a strong thickening effect, whereby the need for monomers is increased and as a result of this the polymerization shrinkage is increased. In addition, the incorporation of the filler is made more difficult by the high viscosity and the maximum amount of filler is limited.

Tooth-filling compositions are known from DE-OS 14 92 040 which contain as filler glass beads with a particle size in the range of 5 to 100 μm. Glass fibres are used in addition to fill intermediate spaces. Because of their spherical shape, the beads are said to guarantee an optimal breaking strength and a low abrasion effect. The colour of the composition is said to automatically match the colour of the natural tooth material upon curing.

DE 24 03 211 A1 discloses dental materials in which exclusively microfine, inorganic fillers (microfillers) on the basis of silicon dioxide are used, the particle size of which is below 700 nm.

According to a particularly preferred version, at least 50 wt.-% of the filler have a particle size of 10 to 400 nm. Surprisingly, filling materials with good transparency and polishability as well as excellent physical properties are obtained.

DE 27 05 220 A1 proposes transparent dental materials with high compressive strength in which a fine-particled filler is used with a grain distribution such that 70–95% of the particles have a grain size of 0.7 to 25 μm and 5–30% of the particles have a grain size of 0.2 to 0.7 μm. Moreover, the filler can contain particles with a smaller diameter than 0.2 μm in an amount of up to 5 wt.-%. The average grain size of the fine-particled fillers is given as 1–5 μm. According to the examples, raw α-quartz is heated and is ground using a specific method.

EP 0 475 239 A2 discloses dental materials which contain as filler a mixture of amorphous, spherical particles of silicon dioxide and up to 20 mol.-% of an oxide of at least one element of groups I; II, III and IV of the periodic system with a refractive index of 1.50 to 1.58 and with an average primary particle size of 0.1 to 1.0 μm, and quartz, glass ceramic or glass powder or their mixtures with a refractive index of 1.50 to 1.58 and with an average particle size of 0.5 to 5.0 μm. The materials are characterized by a high transparency and good polishability.

U.S. Pat. No. 5,356,951 discloses dental materials which contain as filler a mixture of an organic-inorganic composite filler with an average particle size of 5 to 50 μm, glass powder with a maximum particle size of 10 μm and an average particle size of 0.1 to 5 μm and a fine-particled filler with a particle size of 0.01 to 0.04 μm. The composite filler is for its part filled with glass powder which has a maximum particle size of 10 μm and an average particle size of 0.1 to 5 μm. The materials are said to be characterized by a smooth surface, a low polymerization shrinkage and improved physical properties.

DE 198 23 530 A1 discloses dental materials which can contain as filler an organic-inorganic composite material, which has an average particle size of 5 to 50 μm and for its part is filled with an ultrafine inorganic filler with an average particle size of 0.01 to 0.04 μm. The dental materials are polymerized applying pressure and heat and then processed further to dental restorations by milling. These are said to be characterized by good mechanical properties and be free from unpolymerized monomer.

EP 0 983 762 A1 discloses dental materials which contain as filler a mixture of organic-inorganic composite filler with an average particle size of 5 to 50 μm, particular filler with an average particle size of 20 μm or less and optionally glass powder with a maximum particle size of 5 μm and an average particle size of 0.5 to 2 μm. The composite filler is prepared by curing a mixture of a particular filler with an average particle size of 20 nm or less and a methacrylate or acrylate monomer with a viscosity of 60 cP or more and pulverising the cured mixture. The materials are said to be characterized by good polishability and good mechanical properties and have a smoothness and transparency corresponding to the natural tooth.

In spite of the numerous dental materials described in the prior art and in spite of the sometimes significant improvements which were achieved with regard to certain material properties, conventional dental materials mostly still have a polymerization shrinkage of 2.3 to 2.8%. There is thus still a requirement to further reduce the polymerization shrinkage of dental materials without adversely affecting the other properties.

The object of the invention is accordingly to prepare polymerizable compositions which have a low polymerisation shrinkage and good other properties such as transparency and polishability.

This object is achieved by polymerizable compositions which contain a new type of filler on the basis of particulate composite material. This composite filler has an average particle size of 20 to 50 μm and contains at most 10 wt.-% particles with a grain size of <10 μm. The percentage relates to the mass of the composite filler. By a composite material is meant a material on the basis of polymerizable organic binder and inorganic fillers.

Surprisingly it was found that the polymerization shrinkage of polymerizable compositions can be clearly reduced by using composite fillers with the stated grain-size distribution. In addition, the compositions are characterized by good polishability, surface smoothness and abrasion after curing in spite of their comparatively high content of coarse-particled filler.

Basically, composite fillers are preferred which contain as low as possible a proportion of finely particulate material, in particular at most 8 wt.-% and particularly preferably at most 6 wt.-% particles with a size of <10 μm. Composite fillers with an average particle size of 30 to 40 μm are further preferred. The maximum particle size of the composite fillers is preferably 70 μm, i.e. the material contains less than 5 wt.-%, particularly preferably less than 1 wt.-% particles with a size of more than 70 μm.

By average particle size is meant the numerical average, unless stated otherwise. This results from the frequency distribution after grading.

According to the invention, particulate composite materials suitable as composite filler can be prepared for example by mixing organic binder, filler and optionally polymerization initiator, curing and then grinding of the mixture. The ground product is, if necessary, graded, in order to obtain filler with the desired grain-size distribution.

Milling can take place in conventional mills, for example in a ball mill, air-jet mill, impact mill or vibration mill. The composite material can be previously broken down in for example a conical crusher before the actual grinding.

The embodiments show that a considerable proportion of finely particulate material with a particle diameter of <10 μm is formed during normal grinding of composite materials. This is separated according to the invention, for example by grading, such as flow sorting, screening, wind-sifting, optionally in combination with electrostatic processes, flotation, sedimentation, electrostatic or magnetic separation or sieving. Suitable processes are described in Ullmanns Encyklopädie der Technischen Chemie, Volume 2 (1988), Unit Operations.

Suitable as organic binder for the preparation of the particulate composites are all binders curable by polymerization, in particular ethylenically unsaturated polymerizable binders, e.g. monomers, such as monofunctional or polyfunctional methacrylates which can be used alone or in mixtures. Preferred examples of these compounds are methyl methacrylate, isobutyl methacrylate, cyclohexyl methacrylate, tetraethylene glycol dimethacrylate, triethylene glycol dimethacrylate, diethylene glycol dimethacrylate, ethylene glycol dimethacrylate, polyethylene glycol dimethacrylate, butanediol dimethacrylate, hexanediol dimethacrylate, decanediol dimethacrylate, dodecanediol dimethacrylate, bisphenol-A-dimethacrylate, trimethylol propane trimethacrylate, 2,2-bis-[4-(2-hydroxy-3-methacryloxypropoxy)-phenyl]-propane(bis-GMA) as well as the reaction products of isocyanates, in particular di- and/or triisocyanates and OH-group-containing methacrylates. Examples of this are the reaction products of 1 mol hexamethylene diisocyanate with 2 mol 2-hydroxyethylene methacrylate, of 1 mol tri(6-isocyanate-hexyl) biuret with 3 mol 2-hydroxyethyl methacrylate and of 1 mol 2,2,4-trimethylhexamethylene diisocyanate with 2 mol 2-hydroxyethyl methacrylate, called urethane dimethacrylates in the following. The binder content varies between 10 and 80 wt.-% relative to the mass of the composite material, preferably 10 to 30 wt.-%.

Urethane dimethacrylate (UDMA), i.e. the reaction product of 1 mol 2,2,4-trimethylhexamethylene diisocyanate with 2 mol 2-hydroxyethyl methacrylate, 1,10-decanedioldi(meth)acrylate, bisphenol-A-dimethacrylate, ethoxylated bisphenol-A-dimethacrylate and mixtures of these monomers are particularly preferred monomers.

In order to initiate the polymerization, the mixtures contain a polymerization initiator, for example an initiator for the radical polymerization. Depending on the type of initiator used, the mixtures can be polymerized cold, by light or preferably hot.

The known peroxides such as dibenzoyl peroxide, dilauroyl peroxide, tert.-butyl peroctoate or tert.-butyl perbenzoate can be used as initiators for the hot polymerization, but α,α'-azo-bis (isobutyroethylester), benzopinacol and 2,2'-dimethylbenzopinacol are also suitable.

As initiators for the photopolymerization, e.g. benzophenone and its derivatives as well as benzoin and its derivatives can be used. Further preferred photoinitiators are the α-diketones such as 9,10 phenanthrenequinone, diacetyl, furil, anisil, 4,4'-dichlorobenzil and 4,4'dialkoxybenzil. Camphorquinone is particularly preferably used.

2,4,6-trimethylbenzoyldiphenyl phosphine oxide is particularly suitable as initiator for the polymerization initiated by UV light. UV photoinitiators can be used alone, in combination with an initiator for visible light, an initiator for the cold curing and/or an initiator for hot curing.

Photoinitiators are preferably used together with a reducing agent. Examples of reducing agents are amines such as cyanoethylmethylaniline, triethylamine, triethanolamine, N,N-dimethylaniline, N-methyldiphenylamine, N,N-dimethyl-sym.-xylidine and N,N-3,5-tetramethylaniline and 4-dimethylaminobenzoic ethyl ester.

Radical-delivering systems, e.g. benzoyl or lauroyl peroxide together with amines such as N,N-dimethyl-sym.-xylidine or N,N-dimethyl-p-toluidine are used as initiators for the cold polymerization. Dual-curing systems can also be used for catalysis, e.g. photoinitiators with amines and peroxides.

The initiators are normally used in an amount of 0.01 to 5 wt.-% relative to the total mass of the mixture.

Suitable as inorganic filler are in particular quartz, glass ceramic, glass powder cr mixtures of these, preferably glass powder and quite particularly preferably barium glass powder and/or strontium glass powder, the average particle size of these powders preferably being in the range of 0.4 to 1.5 μm and in particular in the range of 0.7 to 1.0 μm. Quartz, glass ceramic and/or glass powder are preferably used in an amount of 10 to 80 wt.-%, in particular 40 to 85 wt.-% relative to the total mass of the mixture.

Moreover, the composite filler can contain fillers for achieving an increased X-ray opacity. The average particle size of the X-ray-opaque filler is preferably in the range of 100 to 300 nm, in particular 180 to 300 nm. Suitable as X-ray-opaque fillers are, e.g. the fluorides described in DE 35 02 594 A1 of the rare earth metals, i.e. the trifluorides of elements 57 to 71. A particularly preferably used filler is ytterbium fluoride, in particular ytterbium trifluoride with an average particle size of approx. 300 nm. The amount of the X-ray-opaque filler is preferably 10 to 50 wt.-%, particularly preferably 20 to 30 wt.-%.

In addition, precipitated mixed oxides, such as for example $ZrO_2/SiO_2$, can be used as fillers. Mixed oxides with a particle size of 200 to 300 nm and in particular approx. 200 nm are preferred. The mixed oxide particles are preferably spherical and have a uniform size. The mixed oxides preferably have a refractive index of 1.52 to 1.55. The mixed oxides can be used as sole filler or in combination with other fillers. The precipitated mixed oxide is preferably used in an amount of 20 to 90 wt.-%, particularly preferably 25 to 75 wt.-% and quite particularly preferably 40 to 75 wt.-%.

The fillers are preferably silanized to improve the adhesion between filler and organic matrix. α-Methacryloxypropyl trimethoxy silane is particularly suitable as adhesion promoter. The amount of the adhesion promoter used depends on the type and the BET surface of the filler.

In addition to the already named substances, the mixtures can contain additives, such as stabilizers and polymerization inhibitors. These are preferably used in an amount of 0.01 to 2 wt.-%.

The total amount of inorganic filler is preferably in the range of 20 to 90 wt.-%, in particular 60 to 88 wt.-% relative to the total mass of the composite filler.

A preferred mixture for the preparation of the composite filler accordingly has the following composition:
(a) 10 to 80 wt.-%, preferably 10 to 30 wt.-% organic binder;
(b) 0.01 to 5 wt.-%, preferably 0.03 to 5 wt.-% and in particular 0.5 to 2 wt.-% polymerization initiator;
(c) 20 to 90 wt.-%, preferably 60 to 88 wt.-% inorganic filler.
As filler (c) the mixture preferably contains
(c1) optionally 10 to 80 wt.-%, preferably 40 to 65 wt.-% glass powder; and/or
(c2) optionally 10 to 50 wt.-%, preferably 20 to 30 wt.-% X-ray-opaque filler; and/or
(c3) optionally 20 to 90 wt.-%, preferably 25 to 75 wt.-%, particularly preferably 40 to 75 wt.-% of precipitated mixed oxide.

All figures relate in each case to the total mass of the mixture. The composition can contain one of the components (c1), (c2) or (c3) or a mixture thereof as filler. Compositions are preferred which contain a filler of type (c1), alone or particularly preferably in combination with one of the components (c2) to (c3).

After curing, grinding and grading, the composite particles are preferably treated with a suitable adhesion promoter. This reacts with the free surface of the filler of the composite material which are exposed when grinding the composite, and thus improves the adhesion between filler and organic matrix. The above-mentioned silanes are preferred as adhesion promoter.

The particulate composite materials according to the invention are particularly suitable as fillers for polymerizable compositions, i.e. compositions which, along with the particulate composite material, contain at least one polymerizable monomer and/or prepolymer and at least one polymerization initiator. The proportion of the particulate composite material is preferably in the range of 20 to 90 wt.-%, particularly preferably 25 to 70 wt.-% and quite particularly preferably 30 to 50 wt.-%. The amount of organic binder is preferably 10 to 80 wt.-%, particularly preferably 10 to 30 wt.-%, the amount of the initiator being 0.01 to 5 wt.-%, in particular 0.1 to 1 wt.-%.

For the preparation of polymerizable compositions, composite fillers with a density of 1.5 to 2.5 $g/cm^3$, in particular 1.8 to 2.2 $g/cm^3$ are preferred. The relatively low density requires a high filler volume proportion in the polymerizable composition and effects an additional decrease of the polymerization shrinkage.

Along with the composite filler, the polymerizable compositions preferably in addition contain further particulate inorganic filler, in particular quartz, glass ceramic, glass powder or mixtures of these, particularly preferably glass powder, quite particularly preferably barium glass powder and/or strontium glass powder. The average particle size of the quartz, glass ceramic and/or glass powder is preferably in the range of 0.4 to 2 μm, particularly preferably 0.4 to 1.5 μm and quite particularly preferably 0.7 to 1.0 μm. The proportion of the quartz, glass ceramic and/or glass powder is preferably 20 to 70 wt.-%, particularly preferably 25 to 50 wt.-% and quite particularly preferably 30 to 40 wt.-% relative to the total mass of the composition.

The compositions can contain moreover one of the above named precipitated mixed oxides and/or one of the above named fillers for increasing the X-ray opacity, such as for example ytterbium trifluoride. The mixed oxide is preferably used in an amount of 20 to 70 wt.-%, the proportion of the X-ray-opaque filler is preferably in the range of 1 to 10 wt.-%, particularly preferably 1 to 5 wt.-%. The particle size of the X-ray-opaque filler is preferably in the range of 100 to 300 nm, in particular 180 to 300 nm. Preferred mixed oxides are precipitated $SiO_2/ZrO_2$-mixed oxides, which preferably have a particle size of 200 to 300 nm and in particular approx. 200 nm.

Moreover, the compositions can contain an organically modified layered silicate for the establishment of the rheological behaviour. The layered silicate is preferably used in an amount of 0.05 to 5 wt.-%, particularly preferably 0.1 to 1 wt.-%. The sum of the proportions of the X-ray-opaque filler and the layered silicate is preferably at most 5 wt.-%.

The total amount of the additional inorganic filler of the polymerizable composition is preferably in the range of 0.05 to 85 wt.-%, in particular 0.1 to 56 wt.-%. According to a particularly preferred version, the polymerizable composition is essentially free from filler with a particle size of <100 nm. The inorganic filler is preferably treated with an adhesion promoter, thus for example silanized.

In addition, the polymerizable compositions can contain normal additive and adjuvants, preferably in an amount of 0.01 to 2 wt.-%.

The substances described above as components of the composite filler are suitable as organic binders, polymerization initiators, additional fillers and additives. Preferred monomers for the preparation of the polymerizable compositions are benzyl methacrylate, ethoxylated bisphenol-A-dimethacrylate, tetrahydrofuryl methacrylate and in particular bisphenol-A-dimethacrylate, ethoxylated bisphenol-A-dimethacrylate according to the formula (1) with n=1 and m=2 and the reaction product of 2 mol hydroxyethyl methacrylate (HEMA) and 1 mol hexamethylene diisocyanate.

Formula (1)

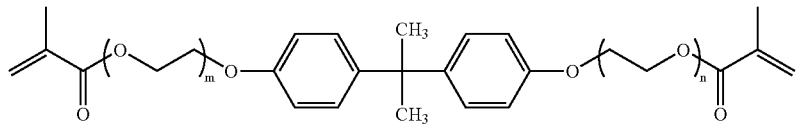

Accelerators, dyes, pigments, UV-absorbers, optical whiteners and lubricants are considered as additives in addition to the above named materials. Compositions which contain a photoinitiator are preferred.

The polymerizable compositions according to the invention preferably have the following composition:
(i) 10 to 80 wt.-%, preferably 10 to 30 wt.-% organic binder;
(ii) 0.01 to 5 wt.-%, preferably 0.1 to 1 wt.-% polymerization initiator;
(iii) 20 to 90 wt.-%, preferably 25 to 75 wt.-% composite filler; and
(iv) optionally 20 to 70 wt.-%, preferably 25 to 50 wt.-% quartz, glass ceramic, glass powder or a mixture of these;
(v) optionally 1 to 10 wt.-%, preferably 1 to 5 wt.-% X-ray-opaque particular filler;
(vi) optionally 20 to 70 wt.-% of precipitated mixed oxide;
(vii) optionally 0.05 to 5 wt.-%, preferably 0.1 to 1 wt.-% layered silicate;
(viii) optionally 0.01 to 2 wt.-% further additives.

The polymerizable compositions are suitable in particular as dental materials. The term dental material is taken to mean tooth-filling materials, materials for inlays or onlays, tooth cements, facing materials for crowns and bridges, materials for false teeth or other materials for prosthetic, preservative and preventive dentistry.

The dental material according to the invention preferably serves as tooth-filling material. Tooth-filling materials are also prepared as two-component materials which cure cold after mixing. The composition is similar to that for the light-curing materials, but instead of the photocatalysts, e.g. benzoyl peroxide is worked into the one paste and e.g. N,N-dimethyl-p-toluidine into the other paste. The result of mixing roughly equal parts of the two pastes is a tooth-filling material which cures fully in a few minutes.

If the amine is left out of the last named materials and e.g. only benzoyl peroxide is used as catalyst, a hot-curing dental material is obtained which can be used for the preparation of an inlay or false teeth. For the preparation of an inlay, an impression is taken of the cavity in the patient's mouth and a plaster mould is prepared. The paste is introduced into the cavity of the plaster model and the whole is polymerized under heat in a pressure pot. The inlay is removed, worked up and then cemented into the cavity in the patient's mouth.

The invention relates not only to the dental material, but also to the finished parts prepared from this, e.g. false teeth, shells, inlays etc.

The invention is explained in more detail in the following using examples.

EXAMPLE 1

Preparation of a Particulate Composite Material (Composite Filler)

Figure 2:
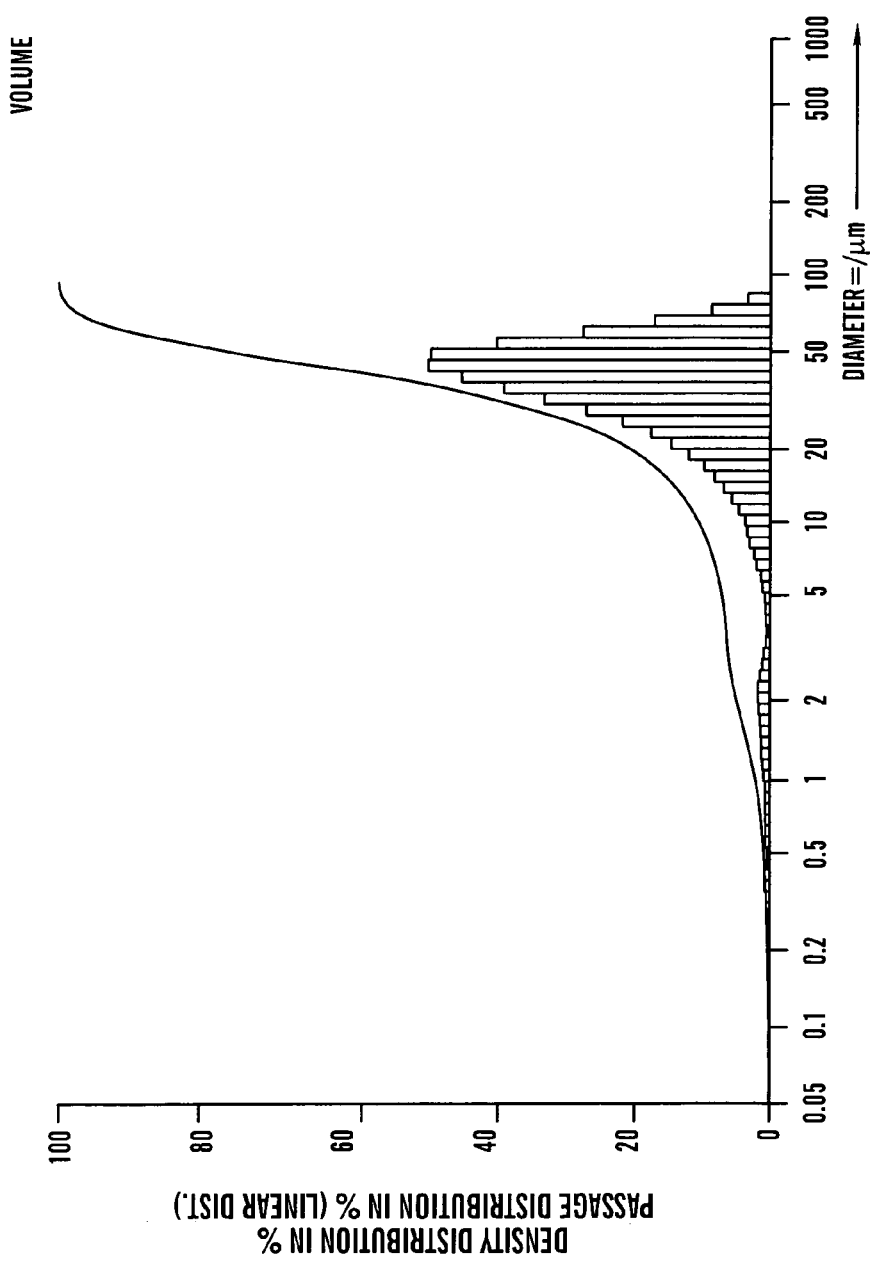

For the preparation of a particulate composite material, the following components were mixed together in the stated amounts, and the mixture cured at 100° C. for 24 hours, then coarsely broken into pieces and then finally ground in a ball mill. The average grain size was 21 µm. The fine (<10 µm) and the coarse (>70 µm) grains were removed by screening. As a result of screening, the average particle size shifts to 37 µm. The grain-size distribution before screening is shown in FIG. 1, the grain-size distribution after screening is shown in FIG. 2. Half of the material was then silanized with 5 wt.-% methacryloxypropyl trimethoxy silane and 2 wt.-% in water.

| Monomer mixture for the preparation of the composite filler: | |
|---|---|
| 1,10-decandiol-dimethacrylate | 30 wt. % |
| Bisphenol-A-dimethacrylate | 39.95 wt. % |
| Urethane dimethacrylate (UDMA) | 27 wt. % |
| Benzoyl peroxide (50%) | 3 wt. % |
| 2,6-di-tert-butyl-para-cresol | 0.05 wt. % |
| Composite filler: | |
| Monomer mixture | 20.5 wt. % |
| Barium glass powder (average particle size 1.0 im) | 54.5 wt. % |
| Ytterbium fluoride | 25.0 wt. % |

EXAMPLE 2

Light-Curing Dental Material (Composite) on the Basis of Composite Filler 39.5 wt.-% of particulate composite material according to example 1 was mixed to a homogenous paste with 39.5 wt.-% barium glass powder with an average particle size of 1.5 µm, 15.5 wt.-% of a monomer mixture with the composition stated below and 2.5 wt.-% of a bentonite paste. The bentonite paste comprises 12.5 wt.-% bentonite (layered silicate) and 87.5 wt.-% of the monomer mixture. To measure the polymerization shrinkage using a dilatometer, 0.1 g of the paste were fixed on a small glass plate, coated with mercury and a distance recorder was placed floating on the mercury. The paste was lit through the small glass plate with a light polymerization apparatus (500 mW/cm$^2$) for 60 seconds. A polymerization shrinkage of 1.6% was measured.

Monomer Mixture for the Preparation of the Dental Material

| polymerizable monomers: | |
|---|---|
| UDMA | 45 wt. % |
| bisphenol-A-dimethacrylate | 33.32 wt. % |
| ethoxylated bisphenol-A dimethacrylate | 20 wt. % |

-continued

| Initiator mixture/stabilizer: | |
|---|---|
| Camphorquinone DL (Photoinitiator) | 0.33 wt. % |
| 4-dimethylamino-benzoic acid-ethylester (accelerator) | 0.6 wt. % |
| 2,4,6-trimethylbenzoyl-diphenyl-phosphine oxide (coinitiator) | 0.4 wt. % |
| 2,2,6,6-tetramethylpiperidine-N-oxide | 0.012 wt. % |
| Additives: | |
| Blue fluorescent pigment (Lumilux Flu blue) | 0.04 wt. % |
| 2-(2'-hydroxy-5'-methylphenyl)-benzotriazole (UV-stabilizer) | 0.3 wt. % |
| Composite | |
| Monomer mixture | 15.5 wt. % |
| Barium glass powder (average particle size 1.5 μm) | 39.5 wt. % |
| Composite filler | 39.5 wt. % |
| Layered silicate paste (12.5 wt. % dispersed in monomer mixture) | 2.5 wt. % |
| Ytterbiumtrifluoride | 3.0 wt. % |

EXAMPLE 3

A light-curing dental material on the basis of the filler according to example 1 was prepared analogously to example 2, but the filler was not freed of fine and coarse grains by screening. Filler of the same batch was used. The polymerization shrinkage was 1.9%.

The invention claimed is:

1. A composition comprising:
 (i) 10 to 80 wt.-% organic binder;
 (ii) 0.01 to 5 wt.-% polymerization initiator;
 (iii) 20 to 90 wt.-% particulate composite filler, comprising a polymerized mixture of organic binder and inorganic filler, the composite filler particles having an average particle size of 20 to 50 μm, each wt-% of (i), (ii), and (iii) relative to the total mass of the composition; and
 wherein the composition contains at most 10 wt.-% composite filler particles having a size of <10 μm, relative to the total mass of the particulate composite filler in the composition.

2. Composition according to claim 1, wherein the composite filler has a maximum particle size of 70 μm.

3. Composition according to claim 1, wherein the composite filler is prepared by curing of a mixture of
 (a) 10 to 80 wt.-% organic binder;
 (b) 0.01 to 5 wt.-% polymerization initiator; and
 (c) 20 to 90 wt.-% inorganic filler, each relative to the total mass of the uncured mixture.

4. Composition according to claim 3, wherein the inorganic filler comprises quartz, glass ceramic, glass powder or a mixture thereof.

5. Composition according to claim 4, wherein said glass powder comprises barium glass powder or strontium glass powder.

6. Composition according to claim 4, wherein said quartz, glass ceramic and/or glass powder has an average particle size of 0.4 to 1.5 μm.

7. Composition according to claim 3, wherein said composite filler contains 10 to 50 wt.-% X-ray-opaque filler.

8. Composition according to claim 7, the composite filler further comprising ytterbium fluoride.

9. Composition according to claim 3, the composite filler further comprising precipitated mixed oxides.

10. Composition according to claim 1, further comprising an inorganic filler which is not a component of the composite filler.

11. Composition according to claim 10, wherein said inorganic filler comprises quartz, glass ceramic, glass powder, or a mixture thereof.

12. Composition according to claim 11, wherein said glass powder comprises barium glass powder and/or strontium glass powder.

13. Composition according to claim 11, wherein said quartz, glass ceramic and/or glass powder has an average particle size of 0.4 to 2 μm.

14. Composition according to claim 10, comprising 25 to 70 wt.-% quartz, glass ceramic and/or glass powder.

15. Composition according to claim 10, further comprising an X-ray-opaque filler which is not a component of the composite filler.

16. Composition according to claim 15, comprising ytterbium fluoride.

17. Composition according to claim 15, comprising 1 to 10 wt.-% X-ray-opaque filler.

18. Composition according to claim 10, further comprising a layered silicate.

19. Composition according to claim 18, comprising 0.05 to 5 wt.-% layered silicate.

20. Composition according to claim 1, further comprising precipitated mixed oxide which is not a component of the composite filler.

21. Composition according to claim 20, comprising $SiO_2$/$ZrO_2$ mixed oxide.

22. Composition according to claim 20, wherein said mixed oxide has a particle size of 200 to 300 nm.

23. Composition according to claim 20, comprising 20 to 70 wt.-% mixed oxide.

24. Composition according to claim 1, further comprising 0.01 to 2 wt.-% additives which are not a component of the composite filler.

25. The composition according to claim 1, comprising a tooth-filling material, material for inlays or onlays, tooth cement, facing material for crowns and bridges, or material for false teeth.

26. Composition according to claim 3, wherein the organic binder is 10 to 30 wt.-%, the polymerization initiator is 0.5 to 2 wt.-%, and the inorganic filler is 60 to 88 wt.-%.

27. Composition according to claim 6, wherein said average particle size is 0.7 to 1.0 μm.

28. Composition according to claim 7, wherein said composite contains 20 to 30 wt.-% X-ray-opaque filler.

29. Composition according to claim 14, comprising 30 to 50 wt.-% quartz, glass ceramic andlor glass powder.

30. Composition according to claim 3, wherein the organic binder comprises 10 to 30 wt.-%, relative to the total mass of the uncured mixture.

31. Composition according to claim 3, wherein the polymerization initiator comprises 0.5 to 2 wt.-%, relative to the total mass of the uncured mixture.

32. Composition according to claim 3, wherein the inorganic filler comprises 60 to 88 wt.-%, relative to the total mass of the uncured mixture.

* * * * *